United States Patent
Koh

(10) Patent No.: US 8,282,562 B2
(45) Date of Patent: Oct. 9, 2012

(54) SYSTEM AND METHOD FOR MONITORING CARDIOPULMONARY FLUID TRANSFER RATES USING AN IMPLANTABLE MEDICAL DEVICE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 840 days.

(21) Appl. No.: 12/411,262

(22) Filed: Mar. 25, 2009

(65) Prior Publication Data

US 2010/0249756 A1 Sep. 30, 2010

(51) Int. Cl.
*A61B 5/08* (2006.01)
*A61B 5/02* (2006.01)

(52) U.S. Cl. ......... 600/484; 600/483; 600/481; 600/506

(58) Field of Classification Search .................. 600/481, 600/483, 484, 504–506, 508, 547; 604/890.1, 604/891.1

See application file for complete search history.

(56) References Cited

U.S. PATENT DOCUMENTS

| | | | |
|---|---|---|---|
| 5,328,460 A | 7/1994 | Lord et al. | |
| 6,480,733 B1 | 11/2002 | Turcott | |
| 6,572,557 B2 | 6/2003 | Tchou et al. | |
| 6,622,045 B2 | 9/2003 | Snell et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,741,885 B1 | 5/2004 | Park et al. | |
| 6,748,261 B1 | 6/2004 | Kroll et al. | |
| 7,149,579 B1 | 12/2006 | Koh et al. | |
| 2007/0055170 A1* | 3/2007 | Lippert et al. | 600/547 |
| 2007/0156061 A1* | 7/2007 | Hess | 600/547 |
| 2008/0262361 A1 | 10/2008 | Gutfinger et al. | |

FOREIGN PATENT DOCUMENTS

EP 1011803 B1 9/2004

* cited by examiner

*Primary Examiner* — Patricia Mallari
*Assistant Examiner* — Tiffany Weston

(57) ABSTRACT

Techniques are provided for use by a pacemaker or other implantable medical device for detecting and tracking trends in cardiopulmonary fluid transfer rates—such as heart-to-lung fluid perfusion rates and lung-to-lymphatic system fluid excretion rates—and for detecting heart failure, dyspnea or other cardiopulmonary conditions. In one example, the device periodically measures transthoracic admittance values. A first exponential time-constant (k1) is determined using curve-fitting from admittance values obtained while the patient is in a sleep posture. Time-constant k1 is representative of the fluid perfusion rate. A second exponential time-constant (k2) is determined based on admittance values obtained while the patient is standing/walking/sitting. The second exponential time-constant (k2) is representative of the fluid excretion rate from the lungs. The device then detects trends, if any, in the time-constants (or in "DC" baseline values) to detect or predict medical conditions such as an imminent heart failure exacerbation.

23 Claims, 11 Drawing Sheets

SYSTEM AND METHOD FOR MONITORING CARDIOPULMONARY FLUID TRANSFER RATES USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for (1) monitoring fluid transfer rates from heart-to-lung and from lung-to-lymphatic system and (2) detecting and tracking heart failure or other medical conditions such as dyspnea based on the fluid transfer rates.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a biventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing."

In view of the potential severity of heart failure, it is highly desirable to predict or detect the condition and to track its progression so that appropriate therapy can be provided. Many patients suffering heart failure are candidates for pacemakers or ICDs. Accordingly, it is desirable to provide such devices with the capability to automatically detect and track heart failure and, in particular, to detect an imminent heart failure exacerbation. Some aspects of the present invention are directed to this end.

Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs, particularly pulmonary venous pressure. The increased pressure pushes fluid—but not blood cells—out of the blood vessels and into lung tissue and air sacs (i.e. the alveoli). This can cause severe respiratory problems and, left untreated, can be fatal. Pulmonary edema can also arise due to other factors besides heart failure, such as infections. Pulmonary edema can result in dyspnea, which pertains to difficult/labored breathing or to shortness of breath.

One therapy delivered to address pulmonary edema and dyspnea is to administer diuretics to the patient in an effort to reduce the amount of fluids within the lungs of the patient. For example, diuretics such as furosemide or bumetanide can be administered to the patient to reduce a pulmonary fluid overload. (Diuretics are drugs that increase the flow of urine, thus eliminating water from the body, ultimately reducing thoracic fluid levels.)

It would also be desirable to provide improved techniques for predicting, detecting and tracking pulmonary edema, dyspnea and related pulmonary conditions and aspects of the invention are directed to this end.

It is particularly desirable to provide techniques that need not be calibrated to individual patients. In this regard, at least some predecessor detection techniques use transthoracic impedance values to estimate left atrial pressure (LAP) within the patient, from which heart failure or pulmonary edema is tracked. These techniques typically require that a conversion procedure (for converting impedance values into estimated LAP values) be calibrated to each individual patient. A technique that does not require calibration would be quite advantageous.

SUMMARY OF THE INVENTION

In accordance with an exemplary embodiment of the invention, techniques are provided for use by an implantable medical device for detecting and tracking trends in cardiopulmonary fluid transfer rates—such as heart-to-lung fluid transfer and lung-to-lymphatic system fluid transfer—and for predicting or detecting heart failure, pulmonary edema, dyspnea or other cardiopulmonary conditions. In one example, a pacemaker or ICD determines a fluid transfer rate representative of at least one form of cardiopulmonary fluid transfer within the patient. The determination is based on admittance, impedance or related electrical signals measured along a sensing vector through a least a portion of lung tissue, such as between a left ventricular (LV) ring electrode to a housing of the device. The device then detects trends, if any, in the fluid transfer rate and controls at least one device function in response to the trends. Such device functions include: generating warning signals indicative of an imminent heart failure exacerbation; controlling delivery of therapy such as diuretics; and controlling the recording of diagnostics.

In an illustrative example, electrical admittance values are measured throughout each twenty-four hour period and, for each value, the device determines whether or not the patient is in a sleep posture (e.g. supine, prone, or lateral) when the value is measured. A posture detector may be used to make this determination. Admittance values obtained while the patient is in a sleep posture are stored as a first set of values for use in determining the rate of transfer of fluids from heart-to-lungs. Admittance values obtained while the patient is not in a sleep posture are stored as a second set of values for use in determining the rate of transfer of fluids from lung-to-lymphatic system.

A first exponential time-constant (k1) is then determined based on the first set of values using curve-fitting. The time-constant (k1) is representative of the rate of transfer of fluids from the left chambers of heart of the patient to the lungs and may be referred to as a fluid perfusion rate. If k1 trends are decreasing over several days, this typically means that fluid transfer from heart-to-lung is slowing due to back fluid pressure from the lung. The k1 rate value is significant in diagnosing the onset of heart failure, especially an increase of left atrial pressure (LAP) associated therewith. A significant decrease in k1 over a period of a few days is deemed to be indicative of an imminent exacerbation of heart failure (which can cause pulmonary edema.)

A second exponential time-constant (k2) is determined based on the second set of values, also using curve-fitting. The time-constant (k2) is representative of the rate of transfer of fluids from the lungs to the lymphatic system and may be referred to as a lymphatic fluid excretion rate. If k2 trends are decreasing over several days, this typically means that there is a back fluid pressure from the lymphatic system as well as the heart, so fluid is not properly removed from the lung. The k2 rate value is significant to diagnosing the onset of dyspnea or shortness of breath, due to lack of alveolar space needed for $CO_2$—$O_2$ exchange.

In the illustrative example, both k1 and k2 can be determined based on admittance values detected throughout the day by fitting a curve of the form:

$$\text{adm}(u,t)=DC+A*(1-u)*(1-\exp(-k1*t))+A*u*\exp(-k2*t)$$

to the values measured throughout a given twenty-four hour period, wherein "DC" represents a minimum detected admittance (Min_Adm) during the period, "A" represents a maximum detected admittance (Max_Adm) during the period minus DC, and u=0 for admittance data collected "at night" and u=1 for admittance data collected "during the day." More generally, u=0 is applied to data collected while the patient is generally in a sleep posture for a sufficient amount of time for admittance to increase significantly, and u=1 is applied for admittance data collected during a subsequent time interval while the patient generally is not in a sleep posture for a sufficient amount of time for admittance to decrease significantly. A significant decrease in either or both of the time-constants (k1, k2) over a period of days is deemed to be indicative of an imminent exacerbation of heart failure. Also, trends in the DC (or "baseline" value) can be tracked. A significant increase in the DC value is indicative of increasing lung congestion.

An important advantage of the illustrative technique is that calibration is not required. That is, the device need not convert admittance/impedance values into calibrated fluid rate values or into calibrated LAP values. Rather, trends in k1 and/or k2 (or in DC) are sufficient to detect fluid transfer problems indicative of heart failure and pulmonary edema.

System and method examples are described in detail below.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
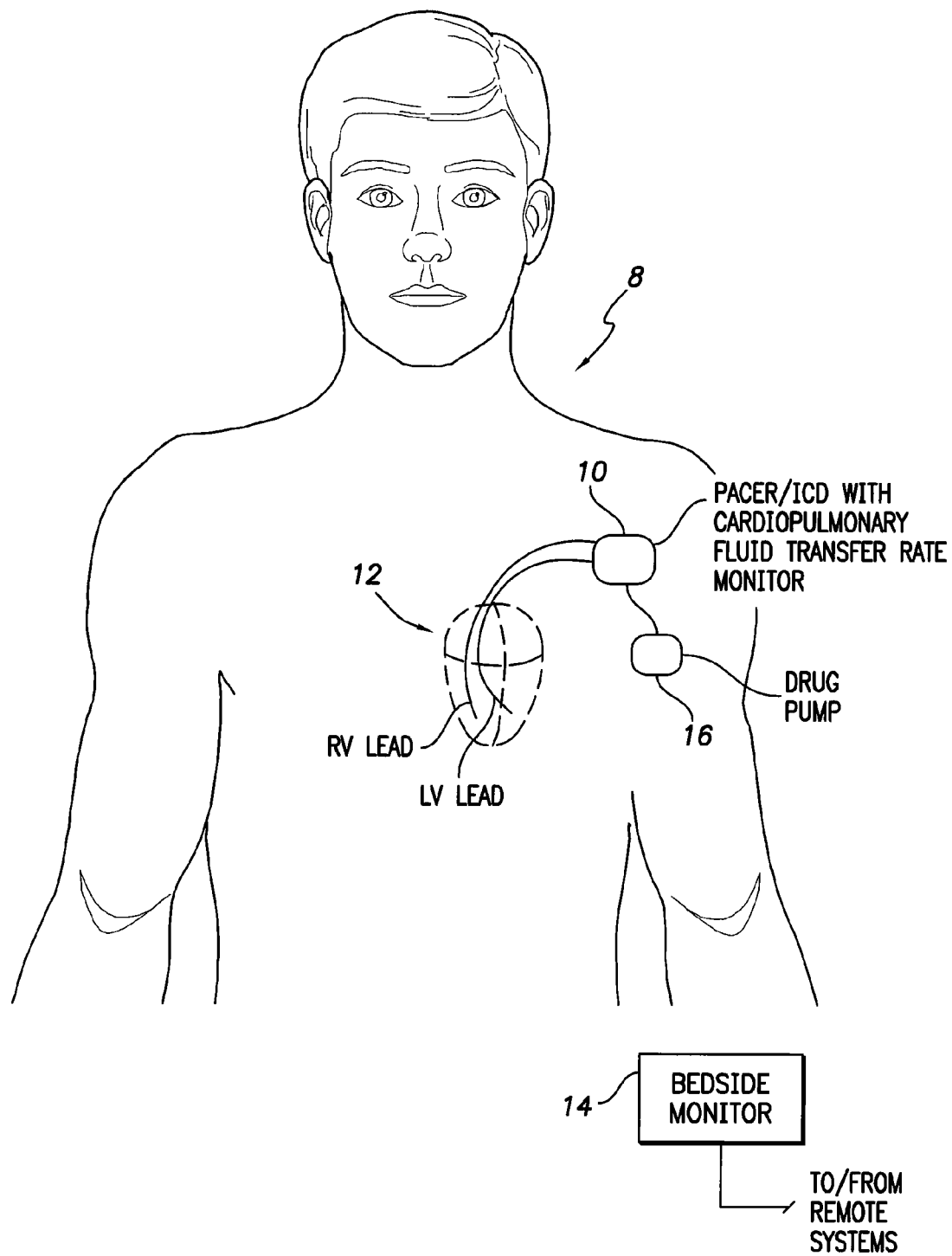
FIG. 1 illustrates pertinent components of an implantable medical system having a pacemaker or ICD capable of determining and monitoring cardiopulmonary fluid transfer rates (including heart-to-lung and lung-to-lymphatic system rates) based on transthoracic admittance measurements.
Figure 2:
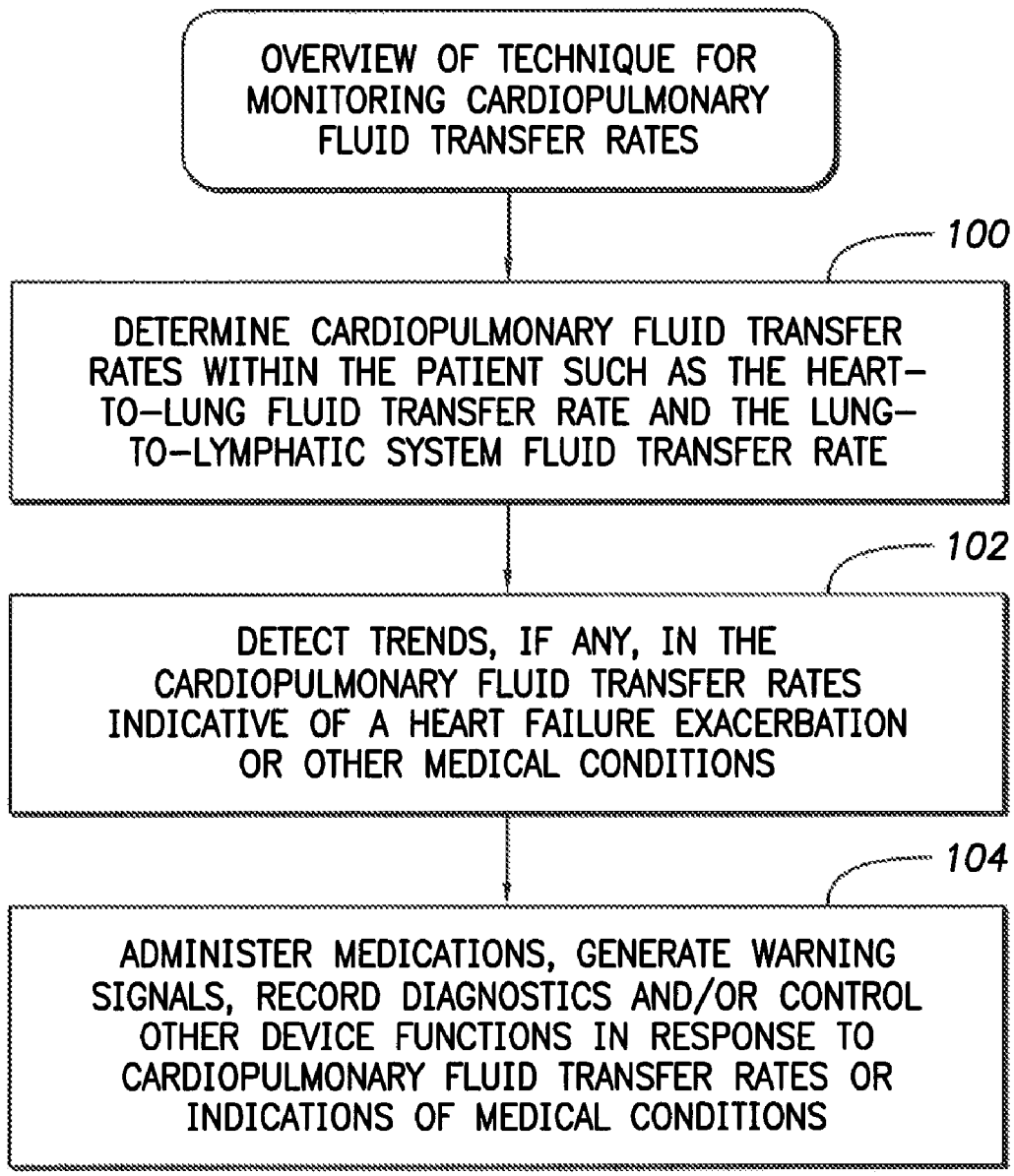
FIG. 2 is a flowchart providing an overview of cardiopulmonary fluid transfer rate monitoring techniques performed by the system of FIG. 1.

FIG. 1 illustrates an implantable medical system 8 capable of monitoring cardiopulmonary fluid transfer rates—including heart-to-lung fluid transfer and lung-to-lymphatic system fluid transfer—and for predicting or detecting heart failure, pulmonary edema, dyspnea or other cardiopulmonary medical conditions. The system is further capable of titrating dosages of diuretics or other medications in response to trends in the fluid transfer rates. To these ends, medical system 8 includes a pacer/ICD 10 or other cardiac rhythm management device capable of applying impedance/admittance detection pulses to patient thoracic tissues (including at least some lung tissues) via one or more cardiac sensing/pacing leads 12 implanted within the heart of the patient. (In FIG. 1, two exemplary leads are shown—an RV lead and an LV lead, in stylized form. A more complete set of leads is set forth in FIG. 10.)

Figure 10:
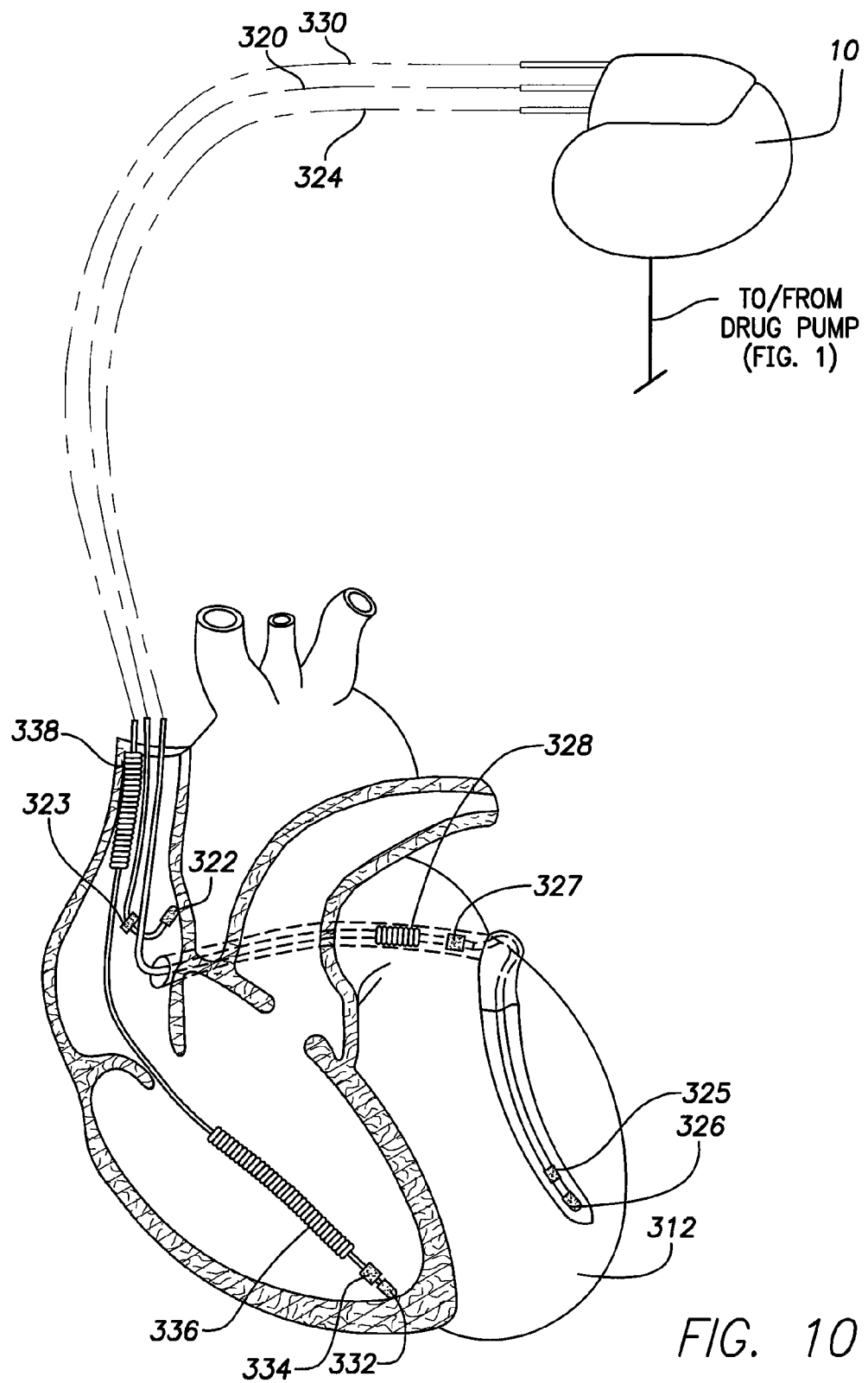
FIG. 10 is a simplified, partly cutaway view, illustrating the pacer/ICD of FIG. 1 along with at set of leads implanted into the heart of the patient.
Figure 11:
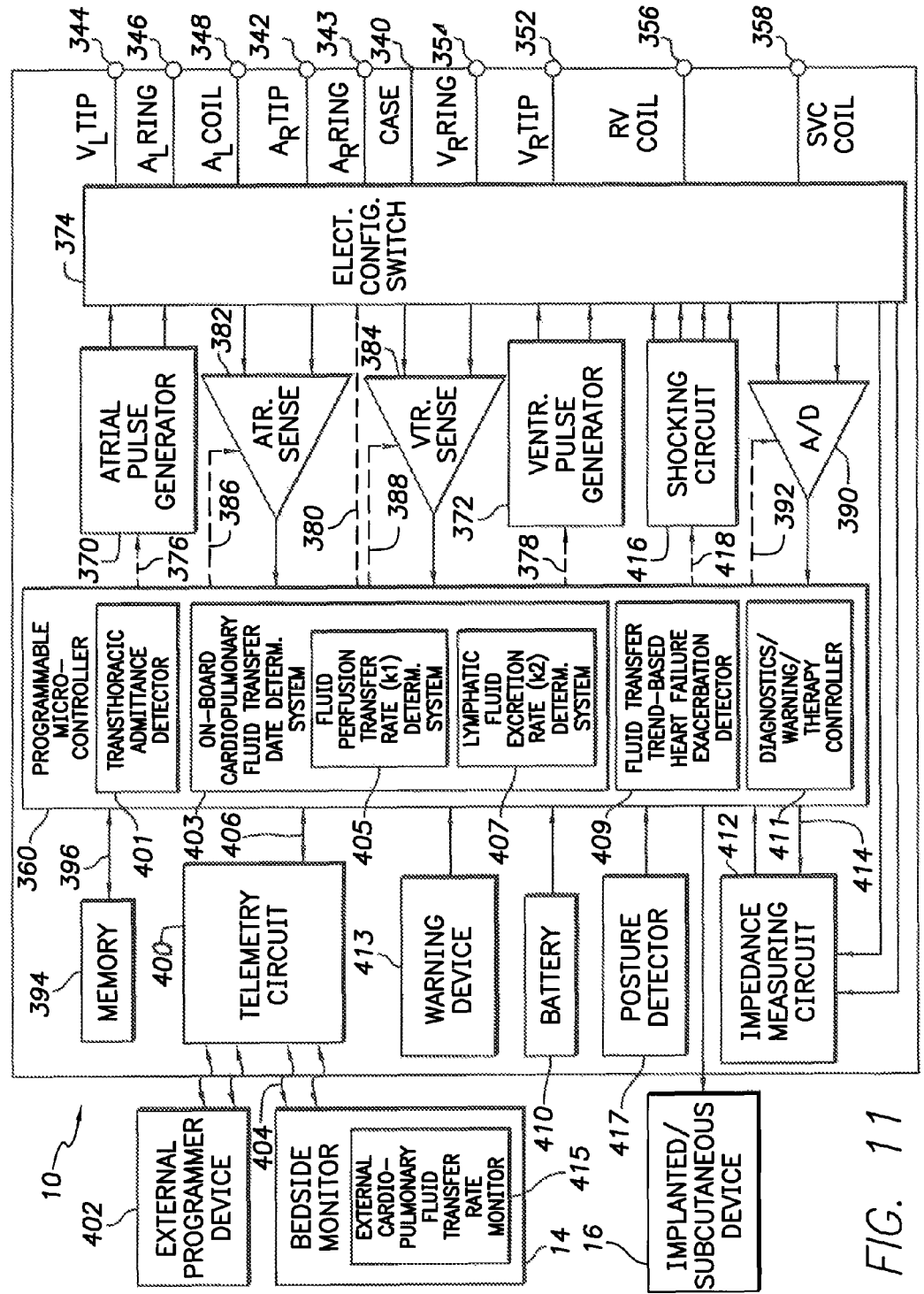
FIG. 11 is a functional block diagram of the pacer/ICD of FIG. 10, illustrating basic circuit elements that provide cardioversion, defibrillation and/or pacing stimulation in the heart and particularly illustrating components for monitoring cardiopulmonary fluid transfer rates using techniques of FIGS. 2-9.

Thoracic impedance/admittance signals are detected based on the impedance detection pulses delivered via the leads, such as pulses delivered between an LV ring electrode and a device housing/can electrode (see FIGS. 10 and 11 for exemplary locations of these electrodes). The pacer/ICD detects and monitors trends in cardiopulmonary fluid transfer rates based on the thoracic impedance/admittance signals using techniques to be described below.

In some embodiments, the pacer/ICD additionally tracks progression of heart failure or pulmonary edema based on long-term trends in the fluid transfer rates. Warning signals may be generated to warn of significant changes in cardiopulmonary fluid transfer rates or other issues using a bedside monitor 14, a hand-held personal advisory module (PAM), not separately shown, or an internal warning device provided within the pacer/ICD. The bedside monitor or PAM may provide audible or visual alarm signals to alert the patient or caregiver, as well as any appropriate textual or graphic displays. The internal warning device (see FIG. 11) may be a vibrating device or a "tickle" voltage device that, in either case, provides perceptible stimulation to the patient to alert the patient.

The bedside monitor may be directly networked with a centralized computing system for immediately notifying a physician or other caregiver of any concerns. The centralized system may include such systems as the HouseCall™ system or the Merlin@home/Merlin.Net systems of St. Jude Medical. A system incorporating bedside monitoring units connected to a centralized external programmer system is described in U.S. Pat. No. 6,622,045 to Snell et al., "System and Method for Remote Programming of Implantable Cardiac Stimulation Devices."

The pacer/ICD may also be programmed to titrate diuretics or other medications in response to trends in the fluid transfer rates. For example, as shown, the implantable system may be equipped with a drug pump 16 or other implantable or subcutaneous drug dispensation device capable of the delivering medications to patient tissues. Implantable drug pumps for use in dispensing medications are discussed in U.S. Pat. No. 5,328,460 to Lord et al., entitled "Implantable Medication Infusion Pump Including Self-Contained Acoustic Fault Detection Apparatus." (This patent also discusses implantable "tickle" warning devices that may be used to deliver warning signals.) In other embodiments, information regarding diuretics is transmitted to an external system, such as to bedside monitor 14, which generates diagnostic displays instructing the patient to take certain dosages of diuretics or other medications.

In addition, diagnostic information pertaining to changes in fluid transfer rates (and to any medical conditions detected therefrom) may be stored within the pacer/ICD for subsequent transmission to an external programmer (see FIG. 11) for review by a physician during a follow-up session between patient and physician. The physician then prescribes any appropriate therapies to address the condition. The physician may also adjust the operation of the pacer/ICD to activate, deactivate or otherwise control any therapies that are automatically applied.

Additionally, the pacer/ICD performs a wide variety of pacing and/or defibrillation functions such as delivering pacing is response to an arrhythmia or generating and delivering defibrillation shocks in response to cardiac fibrillation.

Hence, FIG. 1 provides an overview of an implantable system capable of monitoring cardiopulmonary fluid transfer rates—including heart-to-lung and lung-to-lymphatic system fluid transfer rates—and further capable of titrating medications or controlling other forms of therapy and for delivering appropriate warnings, if needed. Embodiments may be implemented that do not necessarily perform all of these functions. Rather, embodiments may be implemented that only provide, for example, for tracking fluid transfer rates and generating warnings. In addition, systems provided in accordance with the invention need not include all the components shown in FIG. 1. In many cases, for example, the implantable system will include only the pacer/ICD and its leads. Drug pumps are not necessarily implanted. Some implementations may employ an external monitor for generating warning signals but no internal warning device. These are just a few exemplary embodiments. No attempt is made herein to describe all possible combinations of components that may be provided in accordance with the general principles of the invention.

Also, note that, although internal signal transmission lines are shown in FIG. 1 for interconnecting the implanted components, wireless signal transmission may alternatively be employed. The particular shapes, sizes and locations of the implanted components shown in FIG. 1 are merely illustrative and may not necessarily correspond to actual implant locations. Preferred implant locations for the leads are more precisely illustrated in FIG. 10.

Overview of Cardiopulmonary Fluid Transfer Rate Monitoring Technique

FIGS. 2-5 broadly summarize the general technique for monitoring pulmonary fluid transfer rates employed by the system of FIG. 1 or other suitably equipped systems. Beginning at step 100 of FIG. 2, the pacer/ICD determines cardiopulmonary fluid transfer rates within the patient—such as the heart-to-lung fluid transfer rate and the lung-to-lymphatic system fluid transfer rate. This may be performed based on changes in admittance signals derived using transthoracic impedance detection pulses. At step 102, the pacer/ICD detects trends, if any, in the pulmonary fluid transfer rates indicative of heart failure exacerbation or other medical conditions. At step 104, the pacer/ICD administers medications if needed, generates warning signals to notify a clinician, records diagnostics and/or controls other device functions in response to trends in cardiopulmonary fluid transfer rates or any specific indication of heart failure exacerbation.

Figure 3:
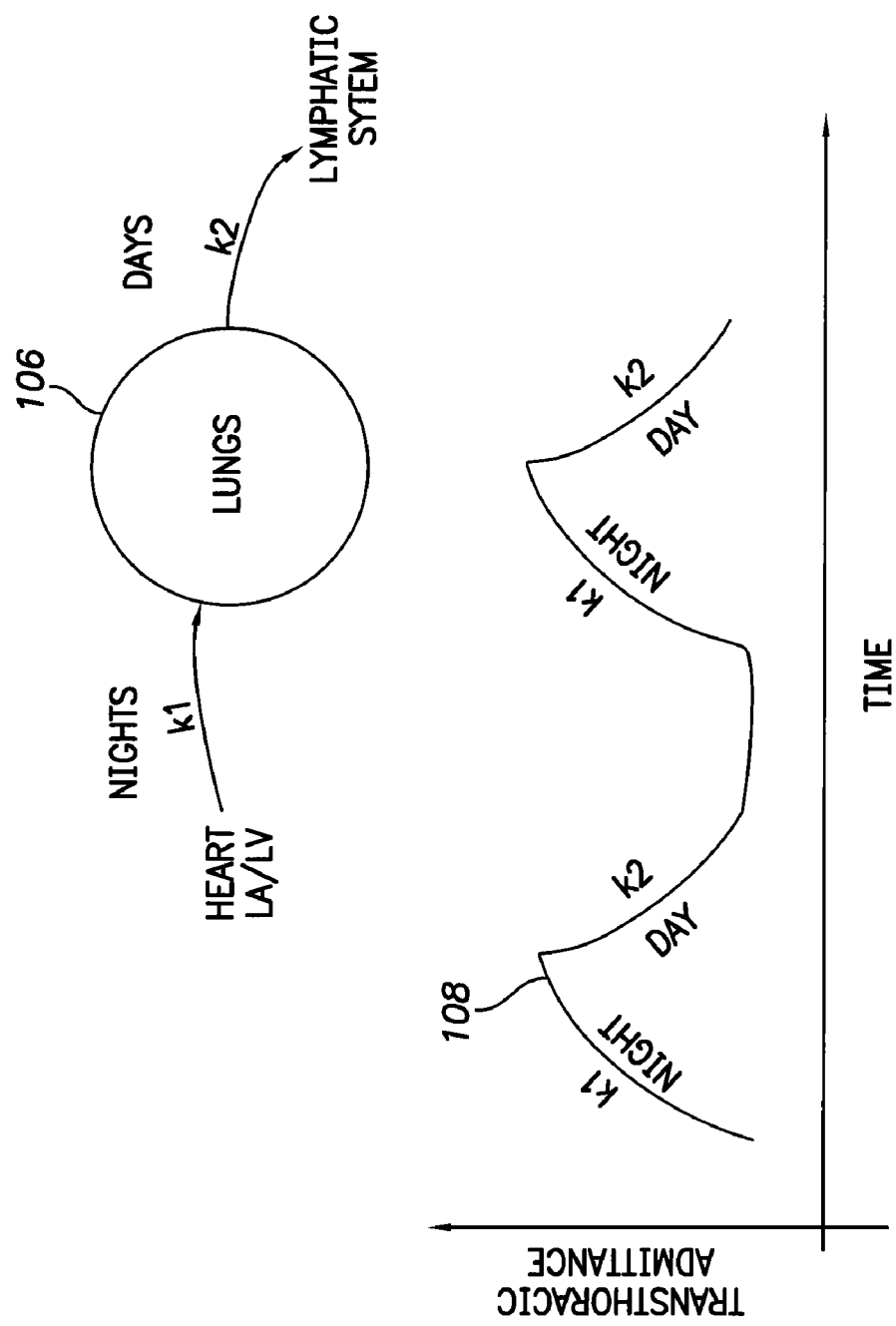
FIG. 3 is a stylized graph illustrating heart-to-lung and lung-to-lymphatic system fluid transfer vectors, as well as corresponding daily variations in transthoracic admittance, which are exploited by the technique of FIG. 2 to evaluate fluid transfer rates.

FIG. 3 graphically illustrates cardiopulmonary fluid transfer, along with exemplary changes in admittance due to the fluid transfer. The lungs of a patient are stylistically represented by circle 106. At night while the patient is typically in a sleep posture (e.g. prone/supine/lateral), fluid transfer proceeds from the left atrium (LA) and left ventricle (LV) of the heart into the lung along vector K1. During the day, while the patient is generally awake and standing or sitting, fluid transfer proceeds from the lungs into the lymphatic system along vector k2. (Although not shown, these fluids eventually return to the LA/LV.) The transference of fluids along these vectors affects transthoracic admittance, as shown by way of admittance graph 108. As can be seen, admittance generally increases during the night as fluids accumulate in the lungs. Admittance then generally decreases during the day as the fluids are withdrawn from the lungs via the lymphatic system.

More specifically, sleep postures increase LAP pressure while non-sleeping postures (i.e. sitting/walking/standing) decrease LAP pressure. Admittance signals measure values representative of the fluid volume in the chest. The fluid perfusion rate (k1) from LV/LA chamber to the lungs in a heart failure patient depends on the differential fluid pressure gradient between LAP and lung pressure. When the lungs are clear of fluid, fluid from LV/LA will transfer to the lungs quickly and k1 will increase to indicate this fast rate. When the lungs have already accumulated fluid, the pressure gradient is weak and therefore the transfer rate is slower (i.e. k1 is smaller). In addition, the baseline or "direct current" (DC) level of the admittance signal will increase. Conversely, the lymphatic fluid excretion rate (k2) determines the removal rate of fluids from the lungs to the lymphatic ducts. Higher k2 indicates faster fluid removal rate from lung-to-lymphatic system. Thus, by observing diurnal trends in k1 and k2, the pacer/ICD can track cardiopulmonary fluid transfer rates and monitor/predict heart failure exacerbation.

Figure 4:
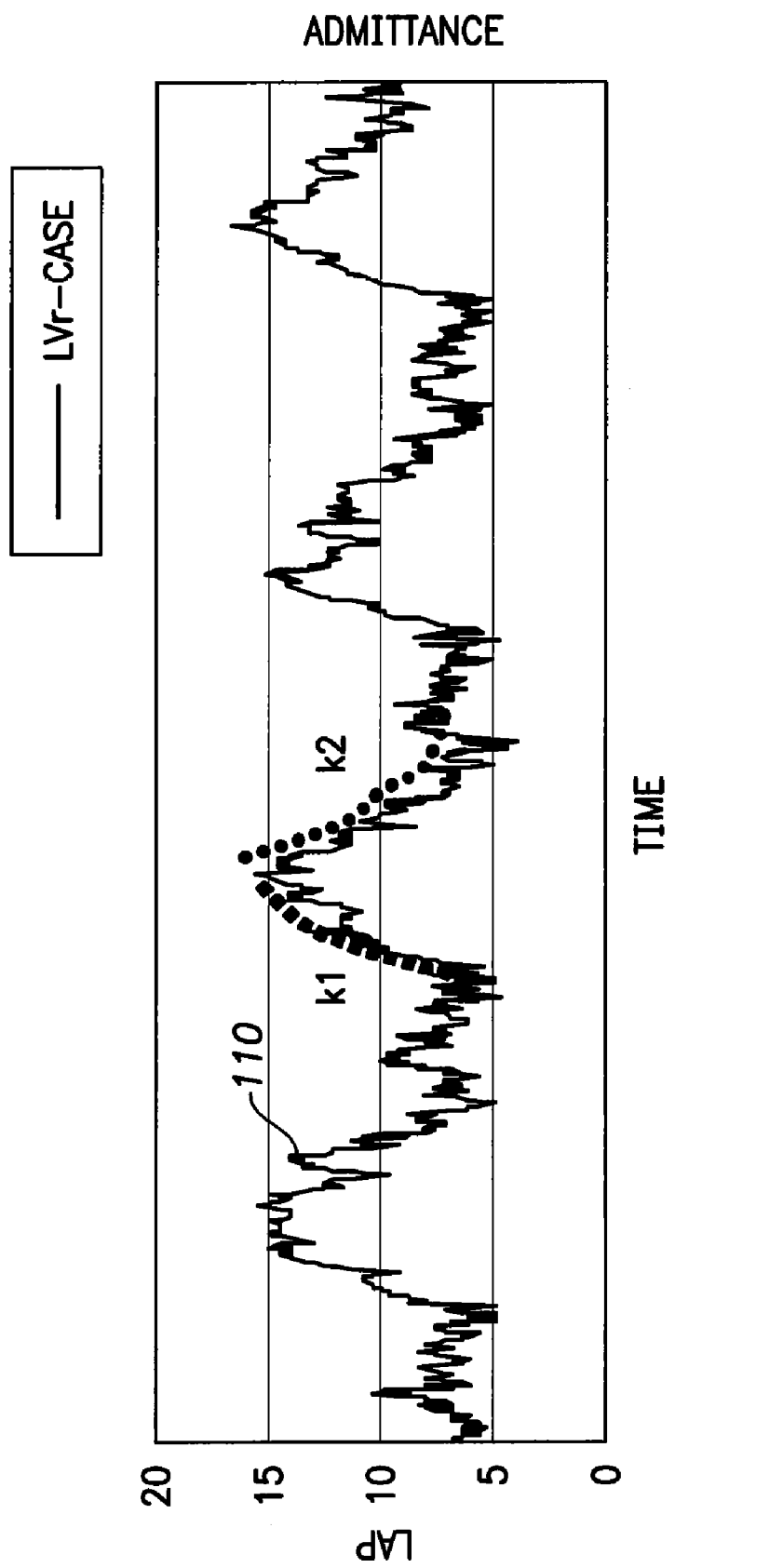
FIG. 4 is a graph illustrating variations in admittance/LAP over a period of several days, which are exploited by the technique of FIG. 2 to evaluate cardiopulmonary fluid transfer rates.

FIG. 4 illustrates about four days of LAP/admittance data obtained via a left ventricular ring (LVr)-can sensing vector. To generate the graph, an initial impedance signal obtained within a human test subject was first converted to admittance and then calibrated to LAP based on a concurrently-measured LAP signal. The LAP values are shown along the left y-axis of the plot. The numerical scale for admittance (in mhos) is not specifically illustrated. The time scale of the graph covers about four days. As can be seen, there is strong diurnal variation in the LAP/admittance signal trace representative of the daily cardiopulmonary fluid transfer trends, as described above. The graph also identifies the fluid perfusion transfer rate (k1) and the subsequent lymphatic fluid excretion rate (k2). Techniques for numerically determining values for k1 and k2 are described below.

Figure 5:
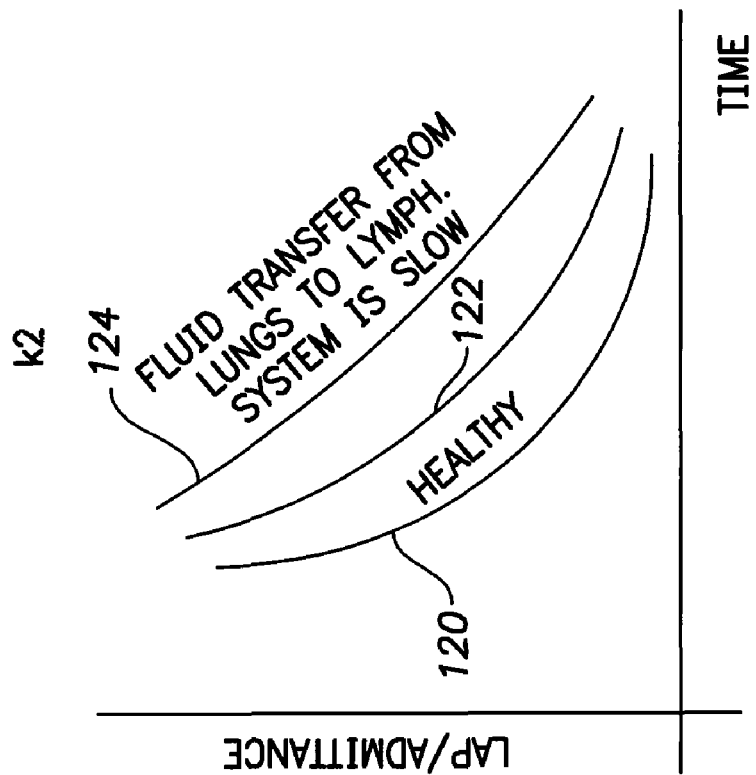
FIG. 5 includes graphs illustrating variations in admittance/LAP contrasting healthy fluid transfer rates with abnormal fluid transfer rates, which may be detected by the technique of FIG. 2.
Figure 5:
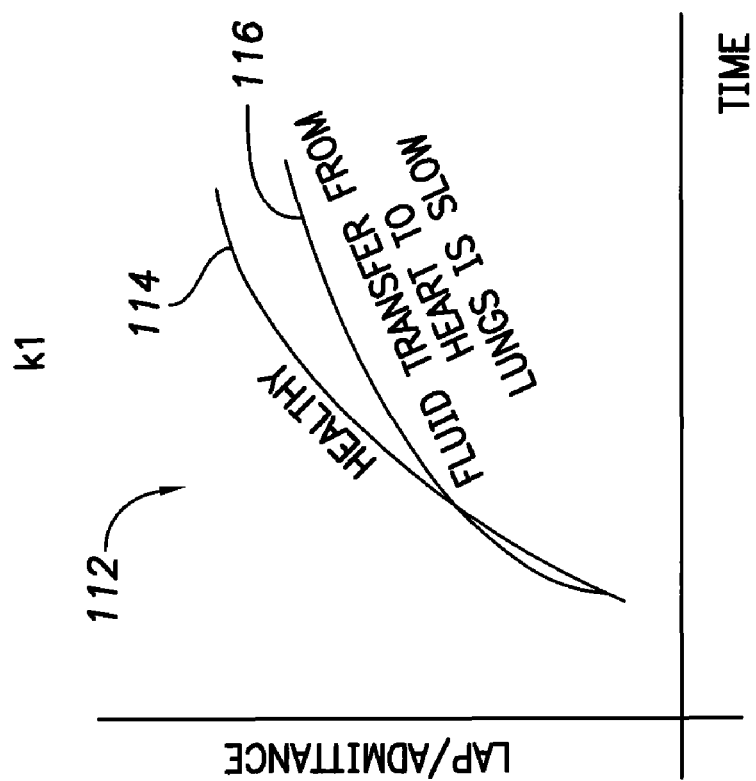
Figure 6:
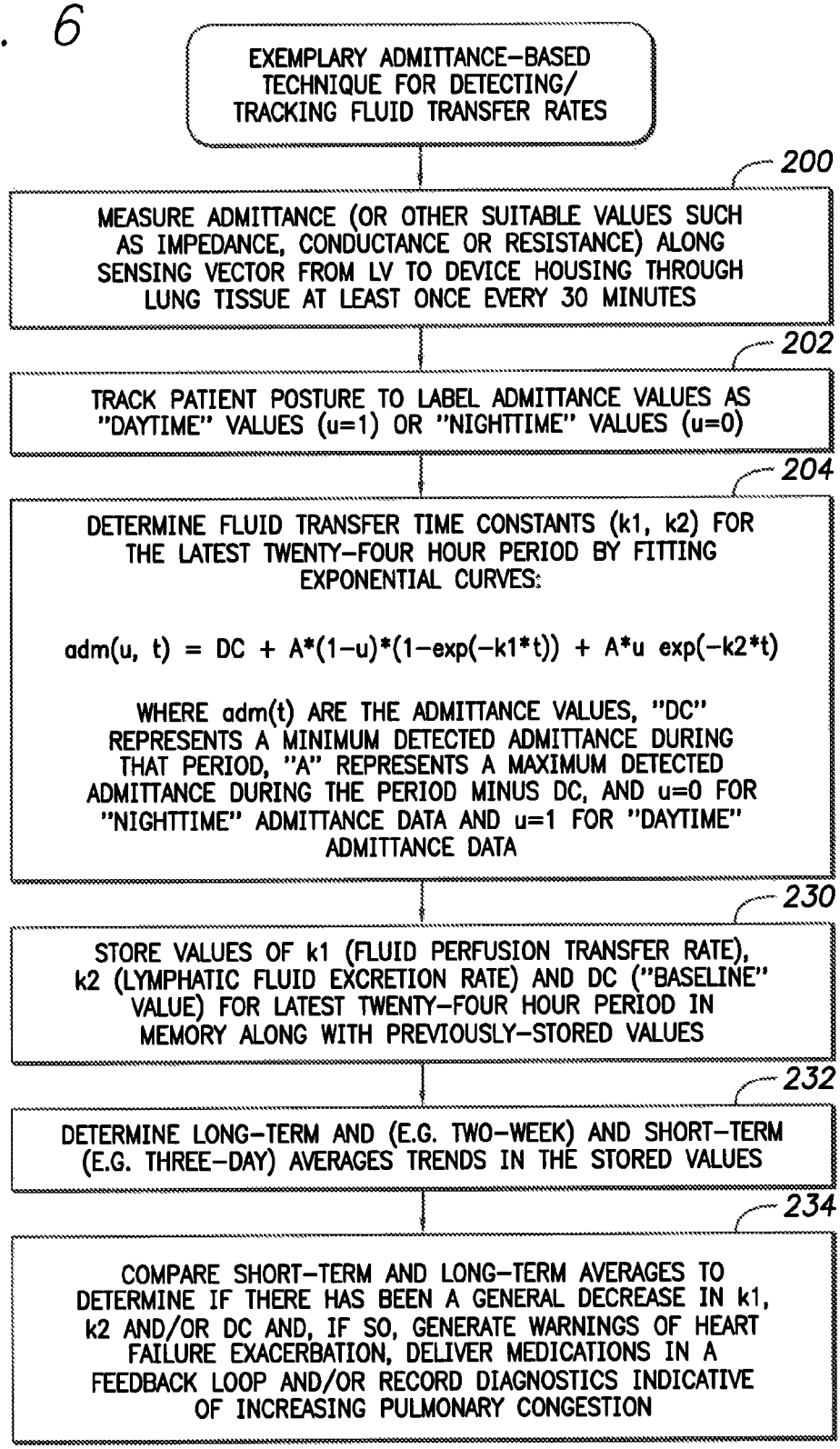
FIG. 6 is a flowchart providing an exemplary technique for determining and monitoring both heart-to-lung (k1) and lung-to-lymphatic system (k2) fluid transfer rates in accordance with the general technique of FIG. 2.

FIG. 5 graphically illustrates healthy and unhealthy fluid transfer rates. Graph 112 includes a pair of increasing LAP/admittance curves indicative of the transfer of fluids from heart-to-lung during a single night. (The units for LAP and admittance are not specifically shown since these values need not be calibrated.) A first LAP/admittance curve 114 shows an increase in LAP/admittance during the night indicative of a healthy transfer of fluids from heart-to-lung. A second nightly LAP/admittance curve 116 shows an increase in LAP/admittance during the night indicative of poor transfer of fluids from heart-to-lung, as can occur within heart failure patients. Note that the k1 value for curve 114 will be greater than that of curve 116 and, as such, a decrease in k1 over a period of days or weeks can be indicative of heart failure exacerbation.

A second graph 118 of FIG. 5 includes a set of three decreasing LAP/admittance curves indicative of transfer of fluids from lung-to-lymphatic system during a single day. A first LAP/admittance curve 120 shows a decrease in LAP/admittance during the day indicative of a healthy transfer of fluids from lung-to-lymphatic system. A second LAP/admittance curve 122 shows a decrease in LAP/admittance indicative of a somewhat poorer transfer of fluids from lung-to-lymphatic system, as can occur within heart failure patients. A third LAP/admittance curve 124 shows a decrease in LAP/admittance indicative of an even poorer transfer of fluids from lung-to-lymphatic system, as can occur with heart failure exacerbation. Note that the k2 value for curve 120 will be greater than that of curve 124 and, as such, a decrease in k2 over a period of days or weeks can also be indicative of heart failure exacerbation, as well as dyspnea. The values of k1 and k2 can also be combined to yield a single metric indicative of overall cardiopulmonary fluid transfer rates.

Thus, FIGS. 2-5 provide a broad overview of a general technique for tracking cardiopulmonary fluid transfer rates and detecting/predicting heart failure exacerbation and other medical conditions. A more detailed example will now be presented.

Exemplary Techniques for Determining K1/K2 and for Predicting HF Exacerbation

FIGS. 6-9 set forth an illustrative technique for tracking cardiopulmonary fluid transfer rates based on transthoracic admittance signals detected by a pacer/ICD. Beginning at step 200 of FIG. 6, the pacer/ICD measures admittance along sensing vector from the LV ring (LVr) to the device housing through lung tissue. In one example, this is performed at least once every thirty minutes throughout each twenty-four hour period. Alternatively, a right ventricular ring (RVr)-to-device housing vector or a right atrial tip (RAt)-to-device housing vector can be used. A combination of vectors can also be employed.

Note that, rather than detecting admittance, other related electrical signals can be exploited, such as impedance, resistance or conductance or their equivalents. Impedance is the numerical reciprocal of admittance and in the context of pacer/ICDs is sometimes referred to as a pulmonary edema (PE) signal, as it can be used to track that condition. Conductance is the numerical reciprocal of resistance. In general, impedance and admittance are vector quantities, which may be represented by complex numbers (having real and imaginary components.) The real component of impedance is resistance. The real component of admittance is conductance. When exploiting only the real components of these values, conductance can be regarded as the reciprocal of impedance. Likewise, when exploiting only the real components, admittance can be regarded as the reciprocal of resistance. Immittance represents either impedance or admittance. Accordingly, herein, "values representative of electrical admittance" encompasses admittance and/or its equivalents.

At step 202, the pacer/ICD tracks patient posture to label each individual admittance value as a "daytime" value (u=1) or as a "nighttime" value (u=0). Any of a variety of posture detectors can be used, alone or in combination with activity sensors. See, for example, U.S. Pat. No. 7,149,579, of Koh et al., entitled "System and Method for Determining Patient Posture based on 3-D Trajectory using an Implantable Medical Device."

Note that, although the terms "daytime" and "nighttime" are used herein for convenience to distinguish periods of time when the patient is generally asleep (i.e. supine/prone/lateral) as opposed to periods when the patient is generally awake (i.e. standing/sitting/walking), it should be understood that these periods of time do not necessarily correspond to actual daytime vs. nighttime intervals, depending upon the particular patient.

At step 204, the pacer/ICD determines the aforementioned fluid transfer time constants (k1, k2) for the latest twenty-four hour period by fitting exponential curves using:

$$\text{adm}(u,t) = DC + A^*(1-u)^*(1-\exp(-k1^*t)) + A^*u^*\exp(-k2^*t) \quad (1)$$

where adm(t) are the admittance values (which generally vary with time (t) during the time period), "DC" represents a minimum detected admittance value (Min_Adm) during the time period, "A" represents a maximum detected admittance value (Max_Adm) during the period minus DC (i.e. A=Max_Adm−Min_Adm), and u=0 for admittance data collected while the patient is in a sleep posture for a sufficient amount of time for admittance to increase significantly and u=1 for admittance data collected while the patient is not in a sleep posture (e.g. standing/walking/sitting) for a sufficient amount of time for admittance to decrease significantly. Otherwise conventional techniques may be applied to fit the data to equation (1). In one example, the pacer/ICD determines a value for k1 based on the night (u=0) data, then separately determines a value for k2 based on the day (u=1) data. To determine k1, for example, the u=0 admittance data for a given twenty-four hour interval may be processed to fit an exponential curve to the data such that a numerical "noise" value is minimized. To determine k2, the u=1 admittance data for the given twenty-four hour interval may be separately processed to fit a different exponential curve to the data, again such that the "noise" value is minimized.

Figure 7:
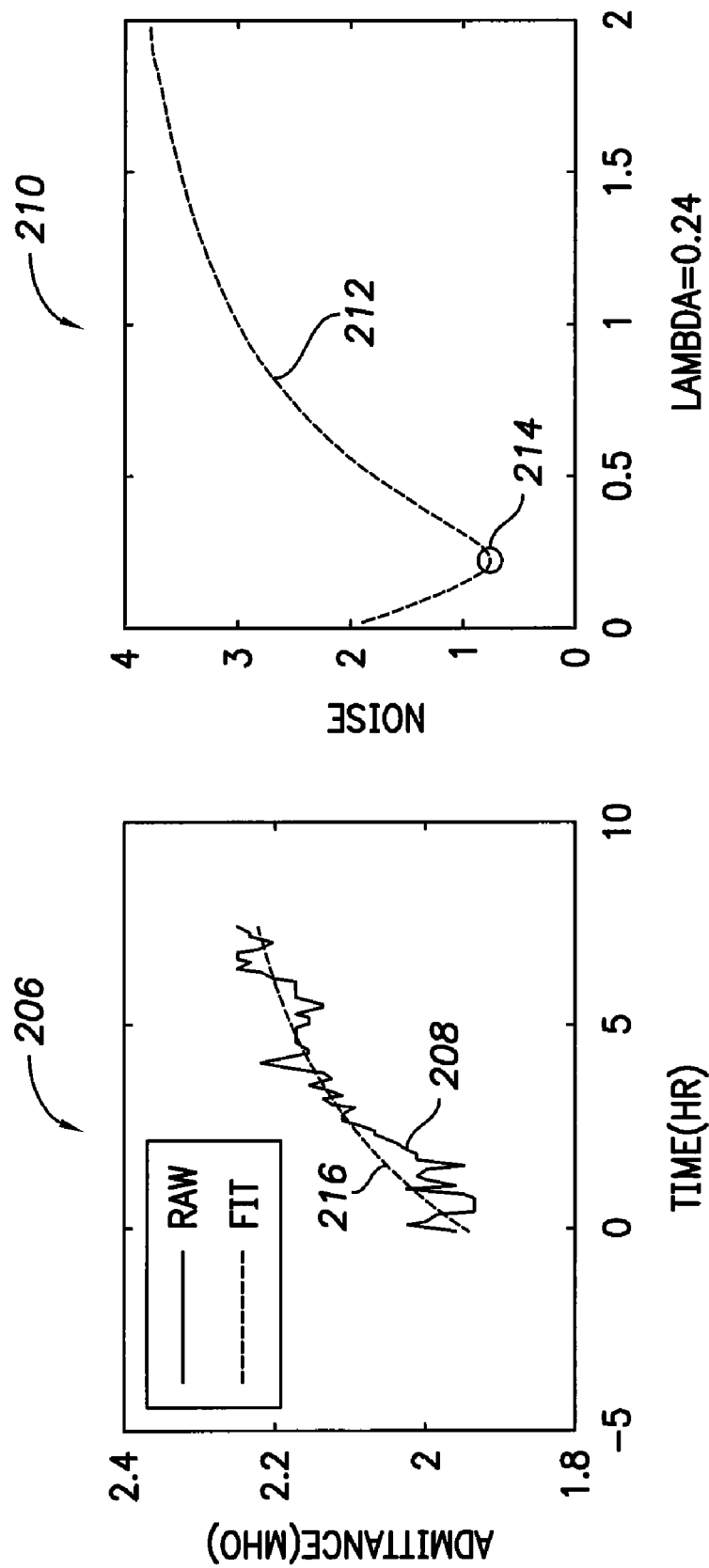
FIG. 7 includes graphs illustrating an increase in transthoracic admittance over a single night and a corresponding lambda value derived from curve-fitting, the latter of which is exploited by the technique of FIG. 3 to represent k1.

FIG. 7 illustrates curve-fitting of exemplary night (u=0) data. A first graph 206 includes a trace 208 illustrating raw admittance data. A second graph 210 illustrates a curve-fitting noise function 212. The minimum value of the function (denoted lambda) indicates the best fit. That is, it is a plot of an amount of error between raw data and fitted data when lambda changes. In this particular example, the best fit is at a value of 0.24, i.e. k1=0.24. The corresponding exponential curve for k1=0.24 is shown as curve 216.

Figure 8:
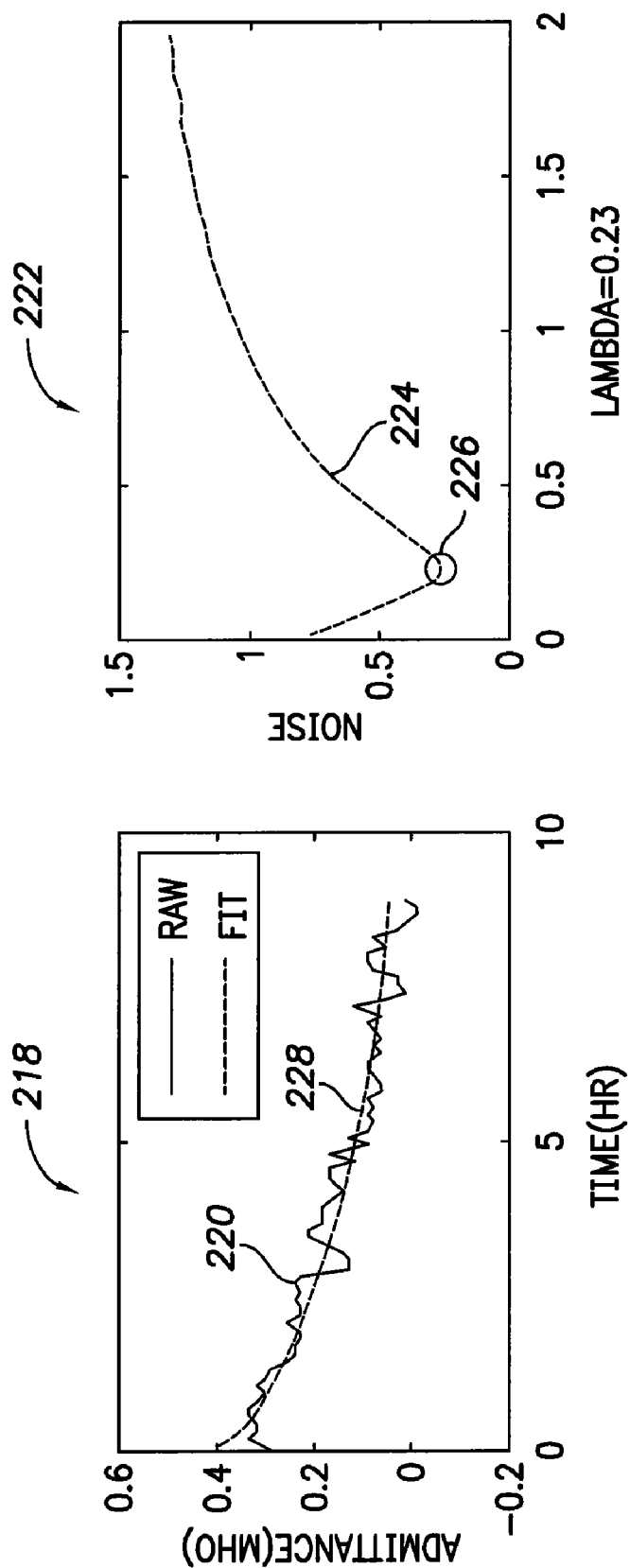
FIG. 8 includes graphs illustrating a decrease in transthoracic admittance over a single day and a corresponding lambda value derived from curve-fitting, the latter of which is exploited by the technique of FIG. 3 to represent k2.

FIG. 8 illustrates curve-fitting of exemplary day (u=1) data. A first graph 218 includes a trace 220 illustrating raw admittance data. A second graph 222 illustrates a curve-fitting noise function 224. The minimum value of the function (denoted lambda) indicates the best fit. In this particular example, the best fit is at a value of 0.23, i.e. k2=0.23. The corresponding exponential curve for k2=0.23 is shown as curve 228.

Returning briefly to FIG. 6, at the pacer/ICD stores the values of k1 (fluid perfusion transfer rate), k2 (lymphatic fluid excretion rate) and DC for the latest twenty-four hour period in memory along with previously stored values. At step 232, the pacer/ICD examines the stored data to determine long-term and short-term averages of the data for comparison. In one example, long-term averages are taken over a period of two or three weeks. Short-term averages are taken over a period of two or three days. Then the pacer/ICD, at step 234, compares the short-term and long-term averages to determine if there has been a general decrease in k1, k2 and/or DC within the patient and, if so, generate warnings of heart failure exacerbation, deliver diuretics or other medications and/or records diagnostics indicative of increasing pulmonary congestion. In some implementations, it may be appropriate to activate or control CRT in response to trends in k1, k2, DC. Depending upon the implementation, the pacer/ICD can separately track trends in k1, k2, DC or can combine the values into a single metric value for tracking. In one example, the pacer/ICD tracks the sum of k1 and k2.

Insofar as titration of medications is concerned, the medications can be delivered by an implantable drug dispensing system in a feedback loop, whereby changes in dosages of medication eventually cause changes in the k1, k2, DC values, which in turn trigger further changes in dosage. In this manner, medications can be adaptively adjusted to keep the k1, k2 and/or DC values within predetermined acceptable bounds, corresponding to acceptable fluid transfer levels and lung congestion levels.

Figure 9:
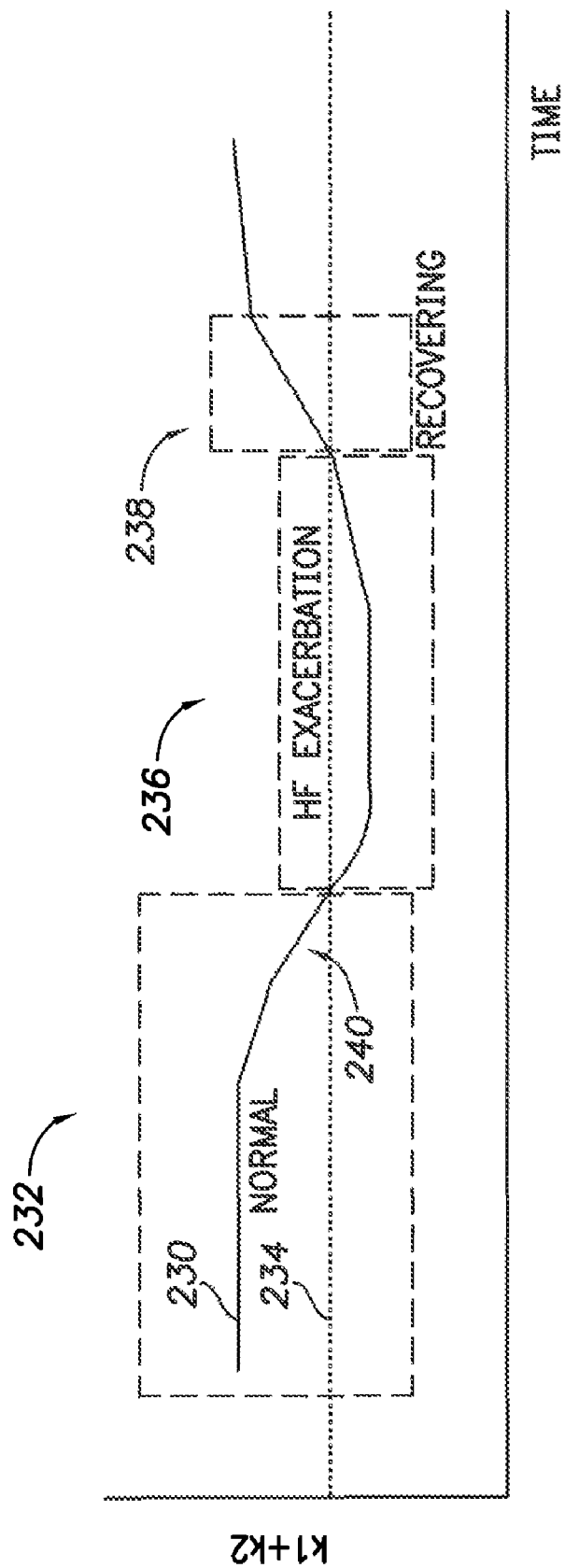
FIG. 9 includes a graph illustrating trends in k1 and k2 exploited by the technique of FIG. 3 to predict or detect heart failure exacerbation.

FIG. 9 illustrates some exemplary trends in a metric value (k1+k2) representative of overall heart-to-lung and lung-to-lymphatic system fluid transfer rates. The value of k1+k2 is shown varying over a period of several weeks by way of line 230. (Note that the graph of FIG. 9 is provided to illustrate features of the invention and does not set forth actual clinically-detected data.) During a first interval of time 232, the fluid transfer rates are generally satisfactory, though the rates begin to decline toward the end of the interval. Once the value of k1+k2 follows below a threshold value 234, a period of heart failure exacerbation 236 is thereby detected. In one example, the threshold is set relative the long-term average (such as a certain percentage below that average, e.g., 20%). The latest short-term average is compared to the threshold and if it falls below the threshold, appropriate action is taken by the pacer/ICD, such as by administering diuretics. Toward the end of interval 236, the value of k1+k2 increases as the patient recovers. Once the value again exceeds the threshold, the patient is then deemed to be in a recovery state 238, and diuretic therapy may then be suspended. Note that, if a percentage-based threshold is used, otherwise routine experimentation can be performed to determine preferred or optimal values for the percentage value to be used. This value may also be programmable by the clinician.

An important advantage of examining trends in k1, k2, DC is that calibration of the values is not required. That is, the device need not convert these values into actual fluid perfusion transfer rates, lymphatic fluid excretion rates, etc. Nor does the device need to convert admittance/impedance values into calibrated LAP values. Rather, trends in k1, k2 and/or DC are sufficient to detect fluid transfer problems indicative of heart failure or other cardiopulmonary conditions.

Additionally, it should be understood that by examining trends in the fluid transfer rate values, the pacer/ICD can sometimes predict a heart failure exacerbation event before it occurs. For example, at time 240, while the fluid transfer rates are steadily decreasing, the pacer/ICD can detect that steady decline and thereby predict the subsequent heart failure exacerbation. In some implementations, the pacer/ICD can then take prophylactic steps to avert the heart failure exacerbation, such as by administering appropriate medications.

Insofar as detecting heart failure or pulmonary edema is concerned, the fluid transfer rate-based techniques of the invention can optionally be supplemented with (or corroborated by) other detection techniques. Alternative techniques for detecting or tracking heart failure are set forth in the following patents: U.S. Pat. No. 6,748,261, entitled "Implantable Cardiac Stimulation Device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure."

Alternative techniques for detecting or tracking pulmonary edema are set forth in following patents or patent applications: U.S. patent application Ser. No. 12/210,848, filed Sep. 15, 2008, entitled "System and Method for Monitoring Thoracic Fluid Levels based on Impedance using an Implantable Medical Device" (A08e1013) and U.S. patent application Ser. No. 11/100,008, filed Apr. 5, 2005, entitled "System and Method for Detecting Heart Failure and Pulmonary Edema based on Ventricular End-Diastolic Pressure using an Implantable Medical Device." See, also, U.S. patent application Ser. No. 12/109,304, filed Apr. 25, 2008, entitled "System and Method for Calibrating Cardiac Pressure Measurements derived from Signals Detected by an Implantable Medical Device."

What have been described are various techniques for determining and exploiting cardiopulmonary fluid transfer rates. For the sake of completeness, a detailed description of an exemplary pacer/ICD for performing these techniques will now be provided. However, principles of invention may be implemented within other pacer/ICD implementations or within other implantable medical devices such as stand-alone cardiopulmonary monitoring devices, CRT devices or CRT-D devices. (A CRT-D is a cardiac resynchronization therapy device with defibrillation capability.)

Furthermore, although examples described herein involve determination of processing of cardiopulmonary fluid transfer rate data by the implanted device itself, some operations may be performed using an external device, such as a bedside monitor, device programmer, computer server or other external system. For example, admittance values detected by the implanted device may be transmitted to the external device, which processes the data to evaluate the fluid transfer rates. Processing by the implanted device itself is preferred as that allows the device to promptly detect or predict the onset of any heart failure exacerbation and to issue prompt warnings or responsive therapy.

In the following section, an exemplary pacer/ICD will be described, which includes components for performing the impedance-based detection and evaluation techniques or FIGS. 2-9.

Exemplary Pacer/ICD

FIG. 10 provides a simplified block diagram of the pacer/ICD, which is a dual-chamber stimulation device capable of treating both fast and slow arrhythmias with stimulation therapy, including cardioversion, defibrillation, and pacing stimulation, as well as capable of performing the impedance-based functions described above. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 10, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 11. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned impedance-based functions.

The housing 340 for pacer/ICD 10, shown schematically in FIG. 11, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 11, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial and ventricular sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart. For arrhythmia detection, pacer/ICD 10 utilizes the atrial and ventricular sensing circuits, 382 and 384, to sense cardiac signals to determine whether a rhythm is physiologic or pathologic. As used within this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 11. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 11, pacer/ICD 10 is shown as having an impedance measuring circuit 412 which is enabled by the microcontroller 360 via a control signal 414. Herein, impedance is detected for use in deriving admittance for use in evaluating fluid transfer rates. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to monitoring cardiopulmonary fluid transfer rates and controlling various device functions based thereon. More specifically, the microcontroller includes a transthoracic admittance detector 401, which derives admittance from impedance signals detected by impedance measuring circuit 412. Also provided is an on-board cardiopulmonary fluid transfer rate determination system 403 operative to determine fluid transfer rates within the patient representative of at least one form of cardiopulmonary fluid transfer, such as heart-to-lung fluid perfusion rates and lung-to-lymphatic system fluid excretion rates. To this end, determination system 403 includes a fluid perfusion transfer rate (k1) determination system 405 operative to determine fluid transfer rates from heart-to-lung. Determination system 403 also includes a lymphatic fluid excretion rate (k2) determination system 407 operative to determine fluid transfer rates from lung-to-lymphatic system. (Additionally, or alternatively, an external cardiopulmonary fluid transfer rate monitor 415 may be provided within bedside monitor 14 or within other external systems to determine cardiopulmonary fluid transfer rates based on admittance/impedance data transmitted from the pacer/ICD. This may be appropriate for use with pacer/ICDs not equipped with an on-board cardiopulmonary fluid transfer rate determination system.) The fluid transfer rate determination system 403 may exploit signals received from a posture detector 417 to determine the current posture state of the patient (i.e. u=0 vs. u=1), as discussed above.

Microcontroller 360 also includes a fluid transfer trend-based heart failure exacerbation detector 409 operative to detect or predict an exacerbation in heart failure, pulmonary edema, dyspnea, and/or related conditions based on trends in the fluid transfer rates. A cardiopulmonary fluid transfer rate-based diagnostics/warning/therapy controller 411 is operative to generate fluid transfer rate-based warnings, control fluid transfer rate-based therapies (such as delivery of diuretics or other medications via implanted/subcutaneous drug pump 16), control the generation of fluid transfer-based diagnostic data and/or control other device functions based on cardiopulmonary fluid transfer rates. In implementations where there is no on-board thoracic fluid monitor, titration of medications is typically achieved by instead providing suitable instructions to the patient or caregiver via the bedside monitor, PAM or other external device. For on-board implementations, diagnostic data may be stored within memory 394 pending transfer to an external system. Warning signals may be relayed to the patient via internal warning device 413 or via bedside monitor 14.

For clarity and simplicity, the internal drug pump is shown in block diagram form with a direct connection to the microcontroller. It should be understood, however, that appropriate electrodes might need to be provided on the device housing to receive/send signals to/from the drug pump.

Depending upon the implementation, the various components of the on-board microcontroller may be implemented as separate software modules or the modules may be combined to permit a single module to perform multiple functions. In addition, although shown as being components of the microcontroller, some or all of these components may be implemented separately from the microcontroller. Depending upon their functions, at least some of the components can exploit or comprise expert systems.

What have been described are various systems and methods for use with a pacer/ICD. However, principles of the invention may be exploiting using other implantable medical systems. Thus, while the invention has been described with reference to particular exemplary embodiments, modifications can be made thereto without departing from the scope of the invention.

What is claimed is:

1. A method for use with an implantable medical device for implant within a patient, said method comprising:
   determining, using a fluid perfusion transfer rate determination system, a fluid perfusion transfer rate representative of transfer of fluids from heart-to-lung within a patient; and
   controlling, using a cardiopulmonary fluid transfer rate-based controller, at least one device function in response to the fluid perfusion transfer rate;
   wherein determining a fluid perfusion transfer rate comprises:
      measuring values representative of electrical admittance through at least a portion of the lungs;
      identifying a first set of values measured while the patient is in a sleep posture;

determining a first exponential time-constant (k1) based on the first set of values; and equating the first exponential time-constant (k1) with the rate of transfer of fluids from heart-to-lung within the patient;

wherein determining a first exponential time-constant (k1) comprises fitting a curve of the form:

$$\mathrm{Adm}(u,t)=DC+A*(1-u)*(1-\exp(-k1*t))$$

to the values measured, wherein "DC" represents a minimum detected admittance during the period, "A" represents a maximum detected admittance during the period minus DC, and u=0 for admittance data collected while the patient is in a sleep posture for a sufficient amount of time for admittance to increase significantly.

2. The method of claim 1 wherein measuring the values representative of electrical admittance through the lungs includes measuring one or more of admittance, impedance, conductance and resistance along a sensing vector from a left ventricular lead to a housing to the device through at least a portion of the lungs.

3. The method of claim 2 wherein measuring the values representative of electrical admittance is performed using one or more of a left ventricular ring (LVr)-to-device housing vector, a right ventricular ring (RVr)-to-device housing vector and a right atrial tip (RAt)-to-device housing vector.

4. The method of claim 1 further including detecting trends in the fluid perfusion transfer rate.

5. The method of claim 4 wherein detecting trends in the fluid perfusion transfer rate includes:

determining a plurality of said first time-constants (k1) over a period of at least two days; and detecting trends in the first time-constants (k1).

6. The method of claim 5 wherein detecting trends in the fluid perfusion transfer rate include detecting a general decrease in the first time-constant (k1).

7. The method of claim 6 wherein controlling at least one device function includes performing one or more of the following in response to a general decrease in the time-constant (k1): generating a warning indicative of the onset of heart failure; controlling delivery of therapy; and controlling a recording of diagnostics.

8. The method of the claim 1 further including detecting a baseline (DC) value from the electrical admittance values and detecting trends in the baseline value.

9. The method of claim 8 wherein said detecting trends comprises detecting an increase in the baseline value which is indicative of an increase in pulmonary congestion.

10. A method for use with an implantable medical device for implant within a patient, said method comprising:

determining, using a lymphatic fluid excretion rate determination system, a lymphatic fluid excretion rate representative of transfer of fluids from lung-to-lymphatic system; and controlling, using a cardiopulmonary fluid transfer rate-based controller, at least one device function in response to the lymphatic fluid excretion rate;

wherein determining a lymphatic fluid excretion rate comprises:

measuring values representative of electrical admittance through at least a portion of the lungs;

identifying a second set of values measured while patient is not in a sleep posture;

determining a second exponential time-constant (k2) based on the second set of values; and equating the second exponential time-constant (k2) with the rate of fluids from lung-to-lymphatic system within the patient;

wherein determining the second exponential time-constants (k2) includes fitting a curve of the form:

$$\mathrm{Adm}(u,t)=DC+A*u*\exp(-k2*t)$$

to the values measured, wherein "DC" represents a minimum detected admittance during the period, "A" represents a maximum detected admittance during the period minus DC, and u=1 for admittance data collected during a subsequent time interval while the patient is not in a sleep posture for a sufficient amount of time for admittance to decrease significantly.

11. The method of claim 10 further including detecting trends in the lymphatic fluid excretion rate.

12. The method of claim 11 wherein detecting trends in the lymphatic fluid excretion rate includes:

determining a plurality of said second time-constants (k2) over a period of at least two days; and detecting trends in the second time-constants (k2).

13. The method of claim 11 wherein detecting trends in the second fluid transfer rate includes detecting a general decrease over time in the second time-constant (k2).

14. The method of claim 13 wherein controlling at least one device function includes performing one or more of the following in response to a general decrease in the time-constant (k2): generating a warning indicative of the onset of dyspnea; controlling delivery of therapy; and controlling recording of diagnostics.

15. A method for use with an implantable medical device for implant within a patient, the method comprising:

determining, using a cardiopulmonary fluid transfer rate determination system, a cardiopulmonary fluid transfer rate within the patient, wherein the cardiopulmonary fluid transfer rate includes both a fluid transfer rate from heart-to-lung and a fluid transfer rate from lung-to-lymphatic system: and controlling, using a cardiopulmonary fluid transfer rate-based controller, at least one device function in response to the cardiopulmonary fluid transfer rate;

wherein determining the cardiopulmonary fluid transfer rates includes:

measuring a set of values representative of electrical admittance through at least a portion of the lungs during at least one twenty-four hour period;

determining a first exponential time-constant (k1) based on values detected while the patient is in a sleep posture;

determining a second exponential time-constant (k2) based on values detected while the patient is not in a sleep posture;

equating the first exponential time-constant (k1) with the rate of transfer of fluids from the heart-to-lung; and equating the second exponential time-constant (k2) with the rate of transfer of fluids from the lung-to-lymphatic system;

wherein determining the first and second exponential time-constants (k1, k2) includes fitting a curve of the form:

$$\mathrm{Adm}(u,t)=DC+A*(1-u)*(1-\exp(-k1*t))+A*u*\exp(-k2*t)$$

to the values measured throughout the twenty-four hour period, wherein "DC" represents a minimum detected admittance during the period, "A" represents a maximum detected admittance during the period minus DC, and u=0 for admittance data collected while the patient is in a sleep posture for a sufficient amount of time for admittance to increase significantly and u=1 for admittance data collected during a subsequent time interval while the patient is not in a sleep posture for a sufficient amount of time for admittance to decrease significantly.

16. The method of claim 15 further including detecting trends in the second fluid transfer rate by:
determining a plurality of said first and second time-constants (k1, k2) over at least two days; and
detecting trends in either one or both of the time-constants (k1, k2) over the period of days.

17. The method of claim 16 wherein detecting trends in the second fluid transfer rate includes detecting a general decrease in a combination of the first and second time-constants.

18. The method of claim 16 wherein controlling at least one device function includes generating a warning indicative of heart failure exacerbation in response to a general decrease in the combination of the first and second time-constants.

19. The method of claim 15 further including detecting trends in the DC value.

20. The method of claim 19 wherein said detecting trends comprises detecting an increase in the DC value which is indicative of an increase in pulmonary congestion.

21. A system for use with an implantable medical device for implant within a patient, the system comprising:
a fluid perfusion transfer rate determination system operative to determine a fluid perfusion transfer rate representative of transfer of fluids from heart-to-lung within a patient; and
a cardiopulmonary fluid transfer rate-based controller operative to control at least one device function based on to the fluid perfusion transfer rate;
wherein the fluid perfusion transfer rate determination system is operative to:
measure values representative of electrical admittance through at least a portion of the lungs;
identify a first set of values measured while the patient is in a sleep posture;
determine a first exponential time-constant (k1) based on the first set of values; and
equate the first exponential time-constant (k1) with the rate of transfer of fluids from heart-to-lung within the patient;
wherein to determine a first exponential time-constant (k1), the fluid perfusion transfer rate determination system is further operative to fit a curve of the form:

$$\text{Adm}(u,t)=DC+A*(1-u)*(1-\exp(-k1*t))$$

to the values measured, wherein "DC" represents a minimum detected admittance during the period, "A" represents a maximum detected admittance during the period minus DC, and u=0 for admittance data collected while the patient is in a sleep posture for a sufficient amount of time for admittance to increase significantly.

22. A system for use with an implantable medical device for implant within a patient, said system comprising:
a lymphatic fluid excretion rate determination system operative to determine a lymphatic fluid excretion rate representative of transfer of fluids from lung-to-lymphatic system within the patient; and
a cardiopulmonary fluid transfer rate-based controller operative to control at least one device function based on the lymphatic fluid excretion rate;
wherein the lymphatic fluid excretion rate determination system is operative to:
measure values representative of electrical admittance through at least a portion of the lungs;
identify a second set of values measured while patient is not in a sleep posture;
determine a second exponential time-constant (k2) based on the second set of values; and
equate the second exponential time-constant (k2) with the rate of fluids from lung-to-lymphatic system within the patient;
wherein, to determine a second exponential time-constant (k2), the lymphatic fluid excretion rate determination system is further operative to fit a curve of the form:

$$\text{Adm}(u,t)=DC+A*u*\exp(-k2*t)$$

to the values measured, wherein "DC" represents a minimum detected admittance during the period, "A" represents a maximum detected admittance during the period minus DC, and u=1 for admittance data collected during a subsequent time interval while the patient is not in a sleep posture for a sufficient amount of time for admittance to decrease significantly.

23. A system for use with an implantable medical device for implant within a patient, said system comprising:
a cardiopulmonary fluid transfer rate determination system operative to determine at least one of a fluid transfer rate from heart-to-lung and a fluid transfer rate from lung-to-lymphatic system; and
a cardiopulmonary fluid transfer rate-based controller operative to control at least one device function based on a cardiopulmonary fluid transfer rate
wherein the cardiopulmonary fluid transfer rate determination system is operative to:
measure a set of values representative of electrical admittance through at least a portion of the lungs during at least one twenty-four hour period;
determine a first exponential time-constant (k1) based on values detected while the patient is in a sleep posture;
determine a second exponential time-constant (k2) based on values detected while the patient is not in a sleep posture;
equate the first exponential time-constant (k1) with the rate of transfer of fluids from the heart-to-lung; and
equate the second exponential time-constant (k2) with the rate of transfer of fluids from the lung-to-lymphatic system;
wherein, to determine the first and second exponential time-constants (k1, k2), the cardiopulmonary fluid transfer rate determination system is further operative to fit a curve of the form:

$$\text{Adm}(u,t)=DC+A*(1-u)*(1-\exp(-k1*t))+A*u*\exp(-k2*t)$$

to the values measured throughout the twenty-four hour period, wherein "DC" represents a minimum detected admittance during the period, "A" represents a maximum detected admittance during the period minus DC, and u=0 for admittance data collected while the patient is in a sleep posture for a sufficient amount of time for admittance to increase significantly and u=1 for admittance data collected during a subsequent time interval while the patient is not in a sleep posture for a sufficient amount of time for admittance to decrease significantly.

* * * * *